US00PP09113P

United States Patent [19]

Newbold, Jr. et al.

[11] Patent Number: Plant 9,113

[45] Date of Patent: Apr. 18, 1995

[54] NEWBOLD'S DIAMOND LEATHERLEAF FERN

[75] Inventors: John R. Newbold, Jr.; William S. Newbold, both of Crescent City, Fla.

[73] Assignee: Jack K. Austin, Umatilla, Fla.

[21] Appl. No.: 165,709

[22] Filed: Dec. 13, 1993

[51] Int. Cl.[6] ..... A01H 5/00

[52] U.S. Cl. ..... Plt./88.3

[58] Field of Search ..... Plt. 88.3

[56] References Cited

PUBLICATIONS

Huxley, A., et al. (Eds.), "Rumohra", *The New R.H.S. Dictionary of Gardening*, Apr. 1992, The Stockton Press, N.Y., pp. 147, 148.

*Primary Examiner*—James R. Feyrer

*Attorney, Agent, or Firm*—Allen, Dyer, Doppelt, Franjola & Milbrath

[57] ABSTRACT

A sport of *Rumohara adiantiformis* (Leather Leaf Fern) is described. The sport is characterized by difference in the fronds, which are denser, much flatter, darker in color, and larger and possess a more pronounced point at their terminal end.

1 Drawing Sheet

BACKGROUND

The present invention describes a new and distinct variety of Leather Leaf Fern that was discovered by us in a ferney owned by Forest Grove Ferneries, Inc., in Crescent City, Fla. At the time of our discovery, we noticed some of the fronds within the fernery exhibited distinct differences with regard to shape, size, and color of the fronds. Upon closer examination, we found that the fronds appeared to be quite different from the parent variety in that they were denser, were much flatter, had a darker color, and were larger with a more pronounced point at their terminal end.

The primary divisions of the frond blade, the pinna, and the secondary divisions, the pinnae, both grow in a markedly more dense pattern than that of the parent, resulting in the visual perception of a more pronounced point.

These features distinguish the sport from varieties of Leather Leaf Ferns with which we are familiar.

Reproduction of the new Leather Leaf Fern variety was performed by choosing a frond having the above-mentioned desirable qualities and separation of the rhizomes. The rhizomes were moved and replanted under a 73% cloth greenhouse at Bill Newbold Ferneries in Crescent City, Fla. The reproduction of the variety has been shown to be consistent by numerous rhizome separations and replantings in ferneries owned by Bill Newbold Ferneries, Forest Groves, Inc. and Lake Ferns, Inc., Umatilla, Fla. A new field has been cultivated and populated with the resulting plants propagated from the chosen frond, the fronds of which have not been commercialized as of the filling date of the present application.

The sport, due to its distinct flatness shape, density, size, and color, tends to be the preferred Leather Leaf Fern of wholesalers who have been shown the results of the propagation of the sport fern. The shape also has been shown to ease the cutting and packing process, since the fronds are flatter, and hence, when picked and packed in bunches, the pinnae experience less breakage. This flatness also causes the fronds to present a denser appearence, and, coupled with the darker coloration, to present a richer appearance, making them more desirable for use in flower arrangements than the parent variety.

DRAWINGS

The accompanying color photograph shows (left) a typical specimen of our new Leather Leaf Fern variety, Newbold's Diamond Leatherleaf Fern, positioned adjacent (right) a typical specimens of Leather Leaf Fern, and in color as nearly as it is reasonably possible to make the same in a color photograph.

DETAILED DESCRIPTION OF THE PLANT

The following is a detailed description of our Leather Leaf Fern variety as based on our observations of specimen plants grown in Crescent City, Fla., with color terminology in accordance with parentage sport of *Rumohra adiantiformis* Leather Leaf Fern.

Parentage: Sport of *Rumohra adiantiformis* (Leather Leaf Fern).

Propagation: Holds its distinguishing leaf shape, flatness, density, and color through succeeding propagation by rhizome separation.

PLANT

This sport is substantially like its parent form in vegetative characteristics, except that when grown in the same amount of light and with the same cultural practices being followed, the leaves are flatter, more dense, and grow to a more pronounced point. Fern colors vary when grown under different conditions and at different growth stages. However, when compared at the same stage and under the same growth conditions, the sport is significantly darker than the parent variety. These visual and physical attributes are caused by the fact that the distance between opposing pinna on the fronds of the new variety is consistently less than the distance between opposing pinna on the fronds of the parent variety. Mathematical analysis of the frond dimensions supports the apparent more dense pattern.

As can be seen in the figure, the distance between opposing pinna of the sport is typically less than that between opposing pinna of the parent, providing a denser appearance. The pinnules generally have the same shape, but are flatter.

The sport grows more slowly than the parent, and generally fewer fronds per acre are produced because of the larger size; a larger frond takes longer to mature.

Origin: Mutation.
Parentage: *Rumohra adiantiformis* (Leather Leaf Fern).
Classification: Polystichum.
Form: Herbaceous.
Height: 16 to 30 inches.
Leaves: One (1) per stem.
Stems: 6 to 12 inches. The stem of the sport tends to the larger than that of the parent.
Foliage: Triangular in shape, one rachis per frond.
Leaf:

*Size.*—8 to 20 inches at the base to 1/16 to ¼ inch at the tips.

*Shape.*—Triangular. The individual leaflets that are a part of the whole are more dense than those of the parent plant and come to a more distinctive point. The leaf of the sport is physically more flat than that of the parent plant.

*Color.*—Forest Green #77×#70, to be distinguished from the parent, which has the color #76. Colors taken from Roehr's Horticultural Color Guide.

I claim:

1. A new and distinct variety of Leather Leaf Fern plant substantially as herein shown and described, characterized by a flat leaf with distinctive dense leaflets on the leaves and a markedly darker green color.

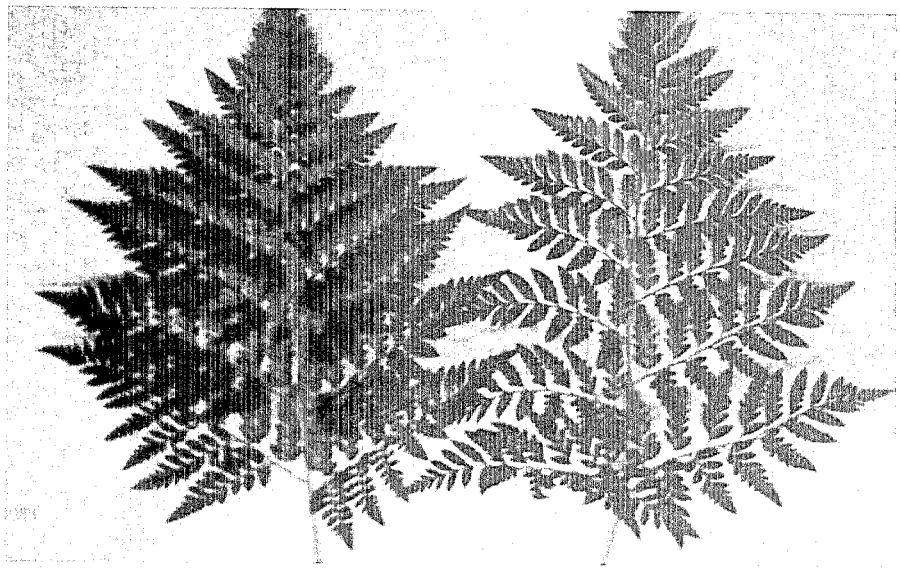

* * * * *